(12) United States Patent
Fuchs et al.

(10) Patent No.: US 7,138,561 B2
(45) Date of Patent: Nov. 21, 2006

(54) COMFORTABLE AND DRY ABSORBENT ARTICLE

(75) Inventors: Christofer Fuchs, Kronberg (DE);
Martin Schnabel, Frankfurt (DE);
Manuela Schneider, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/913,243

(22) Filed: Aug. 6, 2004

(65) Prior Publication Data

US 2005/0033253 A1 Feb. 10, 2005

(30) Foreign Application Priority Data

Aug. 7, 2003 (EP) ................... 03018027

(51) Int. Cl.
*A61F 13/15* (2006.01)
(52) U.S. Cl. ............. 604/378; 604/384; 604/366; 604/367; 604/385.101
(58) Field of Classification Search ............... 604/366, 604/367, 370, 372, 375, 378, 385.101, 384; 442/334, 345, 352, 353, 327, 375; 428/364, 428/394, 395
See application file for complete search history.

(56) References Cited

U.S. PATENT DOCUMENTS 3,860,003 A 1/1975 Buell
4,834,735 A 5/1989 Alemany
5,037,416 A 8/1991 Allen
5,151,092 A 9/1992 Buell
5,269,775 A 12/1993 Freeland
5,509,915 A 4/1996 Hanson et al.
5,527,302 A 6/1996 Endres et al.
5,569,234 A 10/1996 Buell
5,625,222 A 4/1997 Yoneda
5,774,929 A 7/1998 Jurgens
5,997,980 A 12/1999 Matoba et al.
6,004,306 A 12/1999 Robles
6,479,415 B1 11/2002 Erspamer

FOREIGN PATENT DOCUMENTS

| EP | 0 304 319 B1 | 2/1994 |
| EP | 0 752 892 B1 | 7/2001 |
| EP | 1 366 825 A2 | 12/2003 |
| EP | 1 447 066 A1 | 8/2004 |
| WO | WO 98/22279 A1 | 5/1998 |
| WO | WO 99/00098 A1 | 1/1999 |
| WO | WO 00/51651 A1 | 9/2000 |
| WO | WO 03/048440 A1 | 6/2003 |

*Primary Examiner*—Jacqueline F. Stephens
(74) *Attorney, Agent, or Firm*—Jay A. Krebs; George H. Leal; Thibault Fayette

(57) ABSTRACT

Acquisition members having 20 to 40 weight percent of a latex binder and 60 to 80 weight percent of polyester fibers are useful in absorbent articles such as diapers and sanitary napkins. The polyester fibers may further include 20 to 80 weight percent of a first type of fiber, and 20 to 80 weight percent of a second type of fiber, wherein the second type of fiber has spiral-crimped fibers.

13 Claims, 2 Drawing Sheets

COMFORTABLE AND DRY ABSORBENT ARTICLE

FIELD OF THE INVENTION

The present invention relates to absorbent articles such as disposable diapers, sanitary napkins and panty liners. More specifically, the present invention relates to acquisition layers and materials for such acquisition layers, which are very suitable to be used with thin products comprising a relatively high concentration of super-absorbent polymer material.

BACKGROUND OF THE INVENTION

Disposable absorbent articles are broadly available and consumers are used to a high performance for the collecting and retaining of menses (in the case of sanitary napkins or panty liners) or for the collecting and retaining urine and fecal material (in the case of e.g. disposable diapers). However, consumers do not only expect a superior absorbency behavior, but place more and more emphasis on the wearing comfort of such articles.

Typically, such articles comprise multiple absorbent members, at least one member being primarily designed to store liquid, and at least one other member primarily designed to acquire and/or distribute liquid.

At least the storage member will often comprise super-absorbent material, which is admixed with the traditionally used pulp fiber material. Such super-absorbent materials can absorb many times (e.g. 10, 20 or 30 times) their own weight and are therefore very helpful when designing an article of improved fluid handling properties. Many recent products employ higher and higher concentrations of super-absorbent materials, that is concentrations in excess of 50% of the total weight of the storage member. These products achieve a high absorbing capacity with a very thin storage member and are thereby typically overall thin products. While super-absorbent materials can store very large amounts of liquid, they are often not able to distribute the liquid from the point of impact to more remote areas of the absorbent article and to acquire the liquid as fast as it may be received by the article.

For this reason acquisition members are used, which provide for the interim acquisition of large amounts of liquid and which often also allow for the distribution of liquid. Thereby the acquisition member plays a key role in using the whole absorbent capacity provided by the storage member.

An exemplary state of the art absorbent article, namely a sanitary napkin, is disclosed in WO 00/51651. The so-called "secondary topsheet" primarily provides for the liquid acquisition and distribution. The storage member is provided in the form of a core that can contain a high portion of super-absorbent polymer material.

State of the art absorbent articles in the form of disposable diapers are disclosed in the following co-pending applications: EP application no. 02017516.2 and EP application no. 03002677.7. The storage member of these articles may contain more than 50 weight-percent of super-absorbent polymer material, even more than 80% and in some embodiments even about 100% of the super-absorbent polymer material. While these articles are designed to have excellent fluid handling and fluid storage behavior, they may sometimes not be as comfortable to wear as some consumers would like it, namely those consumers interested in a premium product.

For achieving excellent fluid handling and fluid storage properties the respective storage members use super-absorbent materials, which are selected mostly with an emphasis on fluid handling properties. For example EP 304319 B1 (Goldman et al.) discloses the benefits of a relatively narrow distribution of the particle size of the super-absorbent polymers. The respective articles will preferably not comprise many fines, but relatively coarse particles. EP 752892 B1 (Goldman et al.) discloses an absorbent structure, which uses concentrations of super-absorbent particles in access of 60% and teaches to use super-absorbent particles of a relatively high porosity.

Most absorbent articles are designed such that the storage member is facing away from the wearer and such that the acquisition member separates the super-absorbent particles from the wearer. When conceiving the present invention, it was realized that the acquisition layer can play a very important role for imparting wearing comfort to an absorbent article, and namely to an absorbent article comprising a high concentration of relatively coarse super-absorbent particles. Comfort is a challenge in particular for those absorbent articles having a relatively narrow crotch as disclosed for example in U.S. Pat. No. 5,527,302 (Endres et al.) and for articles which are relatively thin as disclosed for example in EP 755649 B1 (Kellenberger et al.).

U.S. Pat. No. 5,997,980 discloses the use of hollow polyester fibers in nonwoven materials which are said to have good thermal recovery.

WO 98/22279 discloses acquisition layers for improved liquid handling in absorbent articles. As a preferred fluid handling material fibrous materials, which are preferably carded are disclosed. These fibers are chemically bonded by a resin. The fluid handling material is designed to achieve an acquisition performance of less than 2 seconds for the third impacting gush of liquid.

WO 99/00098 discloses a fluid acquisition/transfer layer for an absorbent article, which employs thermoplastic multi-component fibers and where the bonding is achieved by the addition of thermoplastic fibers, which are heat bonded.

WO 03/048440 discloses the use of helically crimped single polymer fibers, which preferably are bonded by thermal bonding techniques, in an absorbent article.

It is one objective of the present invention to provide an absorbent article, which has improved liquid handling characteristics as compared to the above disclosed articles.

In one further important aspect it is an objective of the present invention to provide an article, which is more comfortable to wear.

In another aspect of the present invention, it is an objective to provide an article, which is relatively thin and which may have a small crotch region.

SUMMARY OF THE INVENTION

The present invention relates to absorbent articles, such as diapers and sanitary napkins, and acquisition members useful for such articles. More specifically, the invention relates to an acquisition member for an absorbent article, the acquisition member comprising 20 to 40 weight percent of a latex binder, and 60 to 80 weight percent of polyester fibers, wherein the fibers comprise 20 to 80 weight percent of a first type of fibers, and 20 to 80 weight percent of a second type of fibers, the second type of fibers comprising spiral-crimp fibers.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally coexisting. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven", "nonwoven fabric" and "nonwoven web" are used interchangeable.

Absorbent Articles

Figure 1:
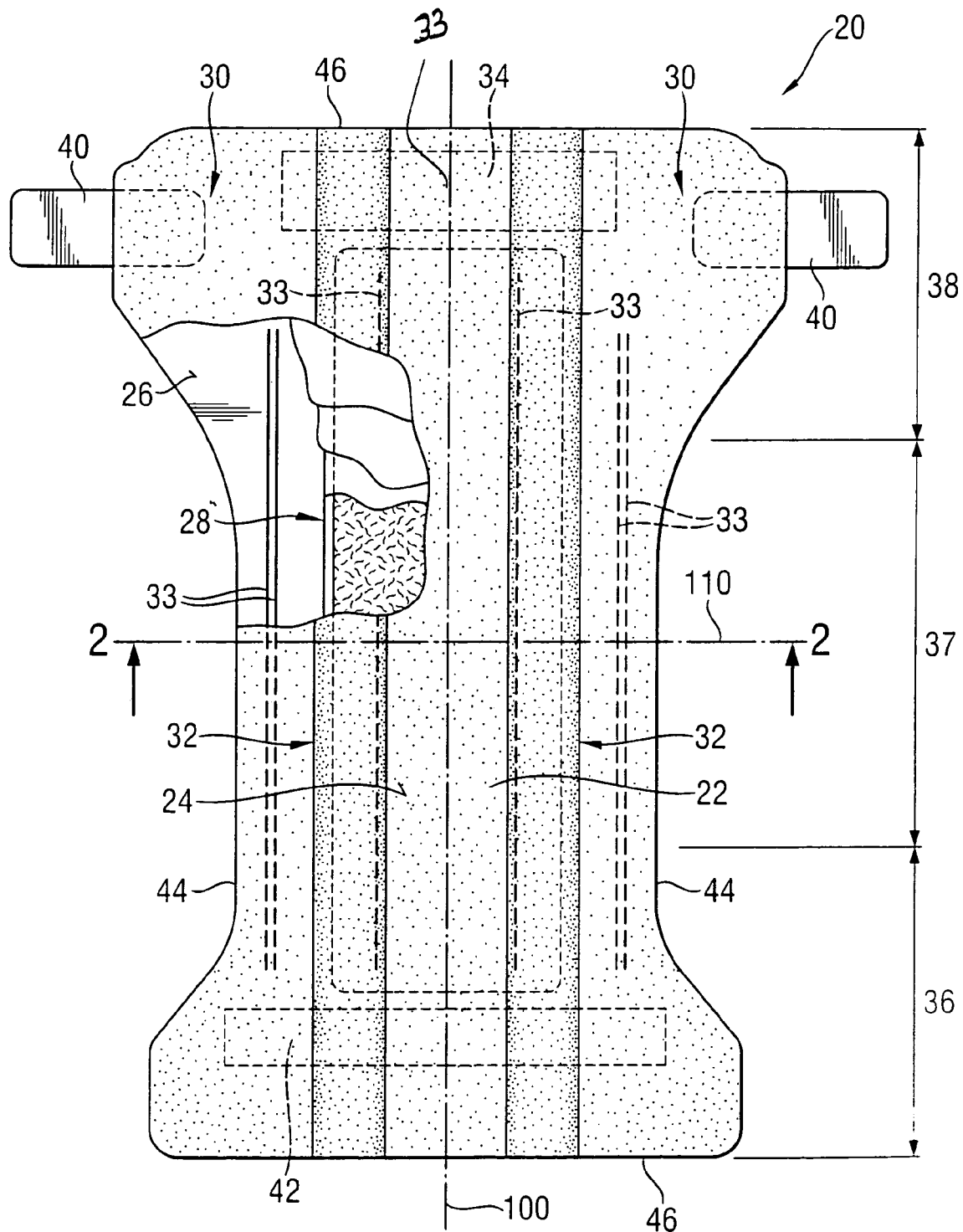
FIG. 1 is a top plan view of a disposable diaper, with the upper layers partially cut away.

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis preferably further includes side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 preferably attached to the rear waist region 38 and a landing zone 42 attached to the front waist region 36. The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 preferably attached to the rear waist region 38. In a preferred embodiment the fastening system further comprises a landing zone 42 attached to the front waist region 36. The fastening member is attached to the front waist region 36, preferably to the landing zone 42 to form leg openings and an article waist.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

Figure 2:
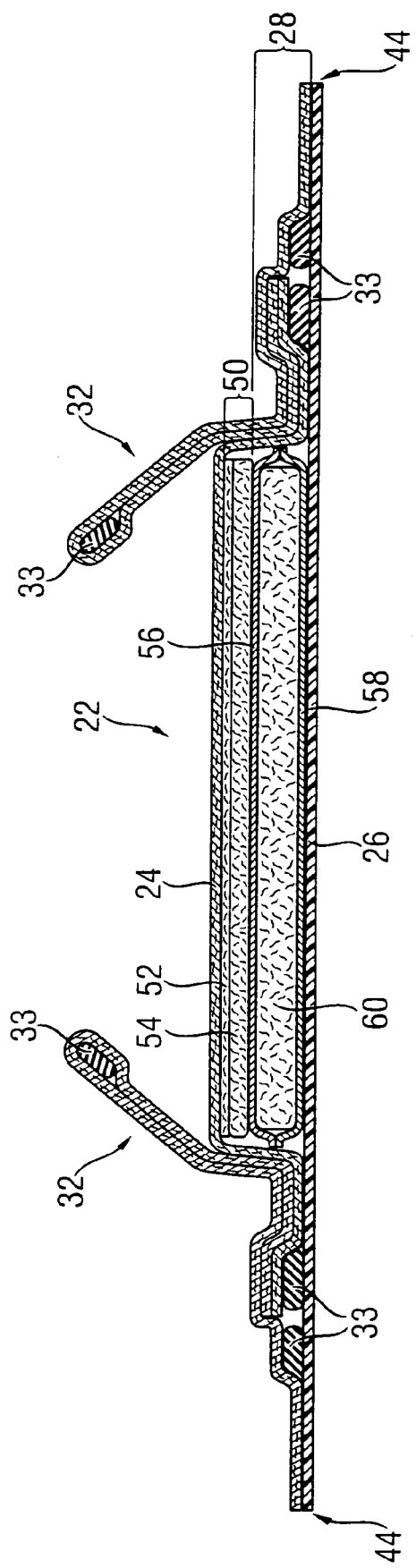
FIG. 2 is a cross-sectional view of the disposable diaper shown in FIG. 1.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core preferably comprises an acquisition system 50, which comprises an upper acquisition layer 52 facing towards the wearer and a lower acquisition layer 54. In one preferred embodiment the upper acquisition layer comprises a nonwoven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer 60.

Acquisition members according to the present invention are preferably comprised by the acquisition system 50 of a diaper as described. Most preferably, the acquisition members are comprised by the upper acquisition layer 52. In one preferred embodiment of the present invention the upper acquisition layer 52 consists of the claimed acquisition member.

The storage layer 60 is preferably wrapped by a core wrap material. In one preferred embodiment the core wrap material comprises a top layer 56 and a bottom layer 58. The top layer 56 and the bottom layer 58 can be provided from a non-woven material. One preferred material is a so-called SMS material, comprising a spunbonded, a melt-blown and a further spunbonded layers. The top layer 56 and the bottom layer 58 may be provided from two or more separate sheets of materials or they may be alternatively provided from a unitary sheet of material. Such a unitary sheet of material may be wrapped around the storage layer 60, e.g. in a C-fold. The top layer 56 and the bottom layer 58 may also be joined to each other, preferably along their periphery. In one preferred option both layers are joined along their longitudinal peripheries, in other embodiments they are joined along the transversal peripheries, or along the longitudinal and the transversal peripheries. The joining can be achieved by multiple means well known in the art, eg. by adhesive means, using a continuous or a discontinuous pattern, and preferably a linear or curvilinear pattern.

The storage layer 60 typically comprises fibrous materials, mixed with superabsorbent, absorbent gelling materials. Other materials described above as suitable for the absorbent core 28 may also be comprised.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibres may be of natural or man-made origin. They may be staple or continuous filaments or be formed in situ.

Nonwoven fabrics can be formed by many processes such as meltblowing, spunbonding, carded. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or non-woven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Example synthetic fibers, which are derived from natural fibers include but are not limited to rayon and lyocell, both of which are derived from cellulose, a natural polysaccharide fiber. Synthetic fibers, which are not derived from natural fibers can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers, which can be laid into webs at a distinctly subsequent point in time. Example direct extrusion processes include but are not limited to: spunbonding, meltblowing, solvent spinning, electrospinning, and combinations thereof typically forming layers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermobonding by use of heated calendar rolls.

All of the above described fibers and manufacturing techniques can be useful for providing an acquisition member according to the present invention.

Preferred Acquisition Members

According to the present invention, the acquisition system and preferable the upper, wearer facing acquisition layer comprises polyester fibers and a latex binder as described hereinafter. Preferred fibers according to the present invention are PET fibers, such as polyester fibers.

The acquisition materials have been found to work best if a blend of different fibers is used. While a blend of 3, 4, 5 or more different fibers can be used, preferably a blend of two fibers is used. Such blend may comprise at least 10, 20, 30, 40, 50, 60, 70, 80, or 90 weight % of a first type and the remaining weight % portion of a second type of fiber. Highly preferred according to the present invention is a 50:50 blend of fibers, i.e. 50 weight percent of a first type of fibers is blended with 50 weight percent of a second type of fibers.

According to the present invention at least the second type of fibers will exhibit a spiral-crimp. As used herein, a spiral-crimp is any three-dimensional crimp and preferably one wherein the fibers substantially assume a helical shape.

Optionally, the first type of fibers may also be spiral-crimped. In one embodiment of the present invention the first type of fibers and the second type of fibers are identical.

The first type of fibers may be thinner than the second type of fibers. Preferably the first type of fibers will have 3–9, more preferably 5–8, and most preferably 6–7 dtex. The second type of fibers will preferable have 8–12, more preferably 9–10 dtex. The first type of fibers and the second type of fibers may be of different length, but preferably are of the same length. Preferably, the fibers have an average length from 20–70 mm, more preferably from 30–50 mm. The first type of fibers will preferably have a higher crimp value as the second type of fibers. Preferred crimp values for the third type of fibers are 8–12 crimps per inch (cpi), and more preferably 9–10 cpi. For the second type of fibers 4–8 cpi are preferred, and 5–7 cpi are even more preferable.

One preferred type of fibers useful in the present invention are so-called bi-component fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). For example, may the intrinsic viscosity of the two materials be different, which has been found to influence the crimping behaviour of the bi-component fibers. Hence, chemically heterogeneous bi-component fibers and chemically homogeneous bi-component fibers are preferred in accordance with the present invention.

Bi-component fibers, which are especially suitable for the second type of fibers are side-by-side bi-component fibers as disclosed for example in WO 99/00098. A specifically preferred type of bi-component fiber is a fiber of circular cross section with a hollow space in the center. It is preferred that 10–15% of the cross sectional area are hollow, more preferably 20–30% of the cross sectional area are hollow.

According to the present invention at least one type of fibers and preferably two or more types of fibers are crimped. For the first type of fibers a 2D crimp or "flat crimp" is preferred. For the second type of fibers a 3D or spiral-crimp is preferred. It is believed that the use of side-by-side bi-component fibers is beneficial for imparting a spiral-crimp to the fibers.

Without wishing to be bound by theory, it is further believed that the spiral crimping of fibers is very beneficial for their liquid acquisition and distribution behavior. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available are important for good liquid distribution and transport. It is further believed that the bi-component spiral-crimped fibers as described above are very suitable to maintain sufficient void volume even when an acquisition member is exposed to pressure. Also are spiral-crimped fibers believed to provide for good permeability as for a given fiber dtex value, the hollow fiber cross-section allows for a larger outer diameter of the fiber as compared to a compact cross-section. The outer diameter of a fiber appears to determine the permeability behavior of an acquisition member formed by such fibers.

While any of the above-described manufacturing processes for non-wovens are suitable to provide an acquisition member in accordance with the present invention, a highly preferred manufacturing process for such an acquisition member in both carding resin-bond technology as described in WO 98/22279. As part of this process the binder will be cured and dried after having been applied to the web.

Nonwoven materials having a basis weight from 20 to 100, preferably from 30 to 80, and most preferably from 50 to 70 gram per square meter are preferred. Basis weight is determined in accordance with the test method described below using a 100 cm long sample of a width given by the role width (but at least 10 cm).

Nonwoven materials useful for acquisition members according to the present invention have a sufficiently high caliper before the article is used, but notably maintain a high caliper even in use conditions when the article is subject to external pressure. Representative caliper measurements are taken at 0.55 kPa (0.08 psi) and at 2.1 kPa (0.30 psi), the latter pressure being thought of being representative for in-use conditions.

Nonwoven materials useful for the present invention will have a caliper from 0.5–5 mm, preferably 1–3 mm, most preferably 1.5–2 mm at a pressure of 0.55 kPa. The caliper of these non-woven materials under a pressure 2.1 kPa will be at least 20%, more preferably at least 30%, and yet more preferably at least 40% of the caliper measured at 0.55 kPa. The caliper at a pressure of 2.1 kPa will also be maintained within the above ranges when the material is in a wetted condition by saturation with saline (0.9 wt % NaCl in deionized water).

The eluate of nonwoven materials according to the present invention has been found to exhibit a low surface tension reduction as compared to the surface tension of saline (0.9 wt % NaCl in deionized water). The eluate of preferred materials will have a surface tension of more than 40, more preferably 50, more preferably 55 and yet more preferably more than 60 mN/m as measured according to the test described herein. A high surface tension appears beneficial for capillary liquid transport when the nonwoven material is used in an absorbent core.

In a further important aspect the nonwoven materials useful for acquisition members in accordance with the present invention have been found to recover well once they have been exposed to pressure. Good recovery denotes the ability of the material to maintain most or a high percentage of its initial caliper after being exposed to relatively high compressive forces. The compression/recovery behavior is tested using the resilience measurement described herein below. Preferred materials in accordance with the present invention will have compression values from 1.4 to 2.2 mm, more preferably 1.7 to 1.9 mm at 0.55 kPa and from 0.8 to 1.5 mm, more preferably from 1.0 to 1.3 mm at 2.1 kPa. Highly preferred materials will exhibit recovery values of at least 50%, 60%, 70%, or 80% of the compression values taken at any pressure used in the resiliency test described below, but preferably at least at a pressure of 0.55 kPa and of 2.1 kPa.

In another important aspect acquisition members made in accordance with the present invention exhibit very high acquisition speeds. Acquisition speed is measured in accordance with the test method disclosed in WO98/22279, entitled "Finished product acquisition test". Preferred materials will achieve an acquisition time of 20–22 seconds (s) for the first gush, 27–29 s for the second gush, 55–58 s for the third gush, and 105–110 s for the fourth gush. It is preferred that the material have a fourth gush acquisition performance from 90–130 s, and preferably from 100–120 s, and more preferably from 105–115 s.

EXAMPLES

Example 1

Disposable Diaper

A disposable diaper exhibiting the benefits of the present invention has been made on the basis of a commercially available product, which is sold as Pampers Active Fit, size 4 in Germany. This product comprises a topsheet, a nonwoven acquisition layer, a cellulosic acquisition distribution layer, a melt blown upper nonwoven core cover material, a storage core comprising airfelt material and super-absorbent polymer material, a lower melt-blown nonwoven core material and a polymeric backsheet (in this order as seen from the wearer facing side).

The disposable diaper has a crotch width of 70 mm and a caliper in the crotch area measured in the crotch area of about 5.5 mm (at 1.38 kPa (0.2 psi)).

The cellulose distribution layer comprises dry-laid chemical stiffened cellulose material and is hourglass shaped. The layer is 248 mm long and has a width of 85 mm in the front and the rear region of the diaper and a width of 65 mm in the crotch region. Cellulose distribution layers with basis weights of 195 gsm, 220 gsm and 250 gsm (gsm=gram per square meter) were found to work well.

The diaper has been tested with different storage cores which all were found to work well. The storage cores had about 65, 70 or 75 weight percent of super-absorbent polymer material. Store cores were prepared having a total of 13, 14 or 15 gram of super-absorbent polymer material.

Super-absorbent polymer materials with a capacity in the range of 28 to 32 g/g and with an Saline Flow Conductivity (SFC) value of 30×, 40 × or 50×$10^{-7}$ $cm^3$ ×s/g. SFC values were determined in accordance with the test method given in U.S. Pat. No. 6,570,058 (C. Fuchs et al.).

In accordance with the present invention the nonwoven acquisition layer has been provided from a 50:50 blend of 6.7 dtex and 10 dtex polyester fibers. The acquisition material comprised 30% styrene-butadiene latex binder (Gen-Flow 3060 as sold by OMNOVA Solutions Inc., Akron, Ohio, USA) and 70% of the described blend of polyester fibers. The first type of fibers having 6.7 dtex were compact-round fibers, exhibiting a 2D crimp, having a length of 38 mm and 9.3 cpi. They are commercially available from Wellmann International Limited, Ireland, and sold under the trade name of Fillwell H1311. The second type of fibers is side-by-side by-component fibers with a hollow/round cross-section and a hollow cross sectional area of 25%. These fibers are spiral-crimped have a length of 60 mm and 6.5 cpi. They are available from Wellmann under the trade name Fillwell H7303. The fibers have been carded into a nonwoven avoiding any fiber or web compression. The binder has been applied homogenously throughout the thickness dimension of the nonwoven. The nonwoven had a basis weight of 60 gsm.

When measured at 0.55 kPa the layer has a caliper of 1.72 mm and a density of 0.03 g/ccm, which results in a void volume of 28.7 ccm/g. When measured at 2.1 kpa in a wet (saline) saturated condition, the material had a caliper of 0.5 mm and a density of 0.03 g/ccm, which corresponds to a void volume of 14.2 ccm/g.

This acquisition layer had a surface tension of 66.6 mN/n.

The compression values for this acquisition material were 1.75 mm at 0.55 kPa and 1.19 mm at 2.1 kPa. The recovery values were 1.37 mm at 0.55 kPa and 0.9 mm at 2.1 kPa.

The diapers have been found to exhibit excellent wearing comfort and dryness.

Example 2

Sanitary Napkin

A sanitary napkin has been prepared in accordance with Example A of WO 00/51651. The secondary topsheet has been replaced by an acquisition layer material as described above under Example 1.

The sanitary napkin has been found to also exhibit excellent wearing comfort and dryness.

Test Methods

Determination of Surface Tension

The surface tension (unit: mN/m) is determined according to the following test.

Apparatus:

Equipment: K10 tensiometer provided by Krüss GmbH, Germany or equivalent. The vessel elevation speed should be 4 mm/min. Liquid surface height should be sensed automatically when using a plate or a ring. The equipment must be able to adjust the sample position automatically to the correct height. Precision of test should be +/−1.0 mN/m.

Procedure:

1. Pouring 40 ml of saline (0.9 wt % NaCl in deionized water) into a cleaned beaker.
2. Testing the surface tension with a platinum ring or a platinum plate. The expected surface tension is 71 mN/m at 20° C.
3. Cleaning the beaker with deionized water and isopropanol and burning it out with a gas burner for a few seconds. Waiting until equilibrate to room temperature is reached.
4. Placing one 60×60 mm piece of test nonwoven into a cleaned beaker. The nonwoven should have a basis weight of at least 10 gsm.
5. Adding 40 ml of saline (0.9 wt % NaCl in deionized water).
6. Stirring with a clean surfactant-free plastic stick for 10 seconds.
7. Letting the solution with nonwoven stand for 5 minutes.
8. Stirring again for 10 seconds.
9. Removing the nonwoven from the solvent with a clean surfactant-free plastic stick.
10. Letting the solution stand for 10 minutes.
11. Testing surface tension of the solution—also referred to as eluate—with a platinum plate or platinum ring.

Density/Caliper/Basis Weight Measurement

A specimen of a defined area such as by cutting with a sample cutter is weighed to at least 0.1% accuracy. If not stated otherwise, caliper is measured under an applied pressure of 550 Pa (0.08 psi) by using a conventional caliper measurement device with a flat plate with a diameter of 2 cm, which can be loaded with defined weights. Where so stated, the same test is run using a higher pressure, typically 2.1 kPa (0.3 psi) which is thought to be representative of in-use conditions. The test specimen can then be placed between this plate and a flat surface and the distance between the plate and the base surface can be measured. The standard caliper measurement is executed by carefully (to avoid over compression) applying a weight of 225 g, resulting in a pressure of 1747 Pa. The weight is left for at least about 5 seconds, upon which the distance reading is taken.

This procedure is repeated at least three times for one specimen to provide a representative number of test data.

The basis weight of a test specimen can be tested by determining sufficiently accurately the weight of a test specimen of known area. Conveniently, a test specimen of 10 cm by 10 cm is weighted e.g. on a scale having an accuracy of 0.001 g.

Basis weight as weight per unit area expressed in g/m2, caliper expressed in mm at 550 Pa pressure, and density expressed in g/cm3 can be readily calculated.

Resiliency Measurement

The resiliency measurement is performed on a stack of sample material by compressing and decompressing it in a dynamometer, such as an Instron instrument.

Samples are prepared at a 70 mm by 70 mm size. A stack of 20 plies of sample material (approximately 3 cm high when uncompressed) is placed between two metal plates, which are larger than the sample size, and which are mounted in a conventional compression/pressure analysis equipment, such as an MTS Alliance RT/1 tensile tester. The instrument is then operated at a crosshead speed of 25 mm per minute in compression and decompression cycles and the displacement pressures are recorded, such as by graphical presentation or in a data file in a connected or internal computer unit.

The equipment is operated in three cycles each between no pressure and up to 6120 Pa (0.7 psi). The corresponding thickness of the 20 plies is noted.

The thickness loss at peak stress (6120 Pa) and thickness loss after stress (0 kPa (0.0 psi)) is recorded by averaging the values as taken from the three cycles, and the relating to the initial caliper as measured according to the method described above.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An acquisition member for an absorbent article, the acquisition member comprising:
   a) 20 to 40 weight percent of a latex binder
   b) 60 to 80 weight percent of polyester fibers, wherein the fibers comprise
      i. 20 to 80 weight percent of a first type of fibers, the first type of fibers comprising spiral-crimp fibers, and
      ii. 20 to 80 weight percent of a second type of fibers, the second type of fibers comprising spiral-crimp fibers, and wherein the first type of fibers has a higher crimp value than the second type of fibers.

2. The acquisition member according to claim 1 wherein the latex binder comprises a styrene-butadiene latex binder.

3. The acquisition member according to claim 1 wherein the first type of fibers comprises hollow chemically heterogeneous bi-component fibers.

4. The acquisition member according to claim 1 wherein the second type of fibers comprises hollow chemically homogeneous bi-component fibers.

5. The acquisition member according to claim 1, wherein the fibers of the first type have 5 to 8 dtex and wherein fibers of the second type have 8 to 12 dtex.

6. The acquisition member according to claim 1, comprising to 40 to 60 weight percent of the first type of fibers and 40 to 60 weight percent of the second type of fibers.

7. The acquisition member according to claim 1, wherein the polyester fibers are carded to form a nonwoven.

8. The acquisition member according to claim 1 having a basis weight of 20 to 100 gsm.

9. The absorbent article, such as a diaper, and incontinence guard, a sanitary napkin, a panty liner or the like comprising an acquisition member according to claim 1.

10. The acquisition member of claim 1 wherein the first type of fibers and the second type of fibers are of the same length.

11. The acquisition member of claim 1 wherein the second type of fibers has a crimp value of 4 to 8 crimps per inch.

12. An absorbent article comprising:
    an acquisition member comprising 20 to 40 weight percent of a latex binder and 60 to 80 weight percent of polyester fibers, wherein the polyester fibers comprise 20 to 80 weight percent of a first type of fibers, the first type of fibers comprising spiral-crimp fibers, and 20 to 80 weight percent of a second type of fibers, the second type of fibers comprising spiral-crimp fibers, and wherein the first type of fibers has a higher crimp value than the second type of fibers; and
    a layer of chemically stiffened cellulose fibers.

13. The absorbent article according to claim 12 said article comprising a topsheet and an absorbent core, the topsheet facing the wearer when said article is in the intended wearing position, said acquisition member and said layer of chemically stiffened cellulose fibers being positioned between the topsheet and the absorbent core.

* * * * *